US008777727B2

(12) United States Patent
Jones

(10) Patent No.: US 8,777,727 B2
(45) Date of Patent: Jul. 15, 2014

(54) TURBO CARD TABLE GAME WITH RFID CARD IDENTIFIER

(71) Applicant: Mark H. Jones, Genoa, NV (US)

(72) Inventor: Mark H. Jones, Genoa, NV (US)

(*) Notice: Subject to any disclaimer, the term of this patent is extended or adjusted under 35 U.S.C. 154(b) by 0 days.

(21) Appl. No.: 13/691,290

(22) Filed: Nov. 30, 2012

(65) Prior Publication Data

US 2013/0137501 A1    May 30, 2013

Related U.S. Application Data

(60) Provisional application No. 61/565,057, filed on Nov. 30, 2011.

(51) Int. Cl.
*A63F 9/24* (2006.01)
*A63F 13/00* (2014.01)
*G07F 17/32* (2006.01)
*A63F 1/12* (2006.01)
*A63F 1/14* (2006.01)

(52) U.S. Cl.
CPC .......... *G07F 17/322* (2013.01); *G07F 17/3293* (2013.01); *G07F 17/3211* (2013.01); *A63F 1/12* (2013.01); *A63F 1/14* (2013.01)
USPC .................... 463/22; 463/11; 463/12; 463/17; 463/31

(58) Field of Classification Search
CPC ............. A63F 1/14; A63F 1/18; A63F 1/067; G07F 17/322; G07F 17/3293
USPC .............................. 463/22, 11, 12; 273/149 R
See application file for complete search history.

(56) References Cited

U.S. PATENT DOCUMENTS

| 1,885,276 | A | * | 11/1932 | McKay | 273/149 R |
| 4,362,303 | A | * | 12/1982 | Pell | 273/274 |
| 4,659,082 | A | * | 4/1987 | Greenberg | 273/149 R |
| 4,667,959 | A | * | 5/1987 | Pfeiffer et al. | 273/149 R |
| 5,605,334 | A | * | 2/1997 | McCrea, Jr. | 273/309 |
| 5,676,372 | A | * | 10/1997 | Sines et al. | 273/149 R |
| 5,722,893 | A | * | 3/1998 | Hill et al. | 463/47 |
| 5,779,546 | A | * | 7/1998 | Meissner et al. | 463/25 |
| 6,217,447 | B1 | * | 4/2001 | Lofink et al. | 463/12 |
| 6,267,671 | B1 | * | 7/2001 | Hogan | 463/25 |
| 6,460,848 | B1 | * | 10/2002 | Soltys et al. | 273/149 R |
| 6,676,517 | B2 | * | 1/2004 | Beavers | 463/25 |
| 7,341,254 | B2 | * | 3/2008 | Loewenstein et al. | 273/292 |

(Continued)

*Primary Examiner* — Steven J Hylinski
(74) *Attorney, Agent, or Firm* — Dickinson Wright PLLC

(57) ABSTRACT

An improved table game system includes a first shuffling machine for randomly selecting a first card from among a first defined set of cards. The system also includes a second shuffling machine for randomly selecting a second card from among a second defined set of cards. A first card reader is associated with the first shuffling machine for communicating with the selected card to obtain relevant information thereabout. A second card reader is associated with the second shuffling machine for communicating with the selected card to obtain information thereabout. The system includes a first display in communication with the first card reader to display the obtained information about the first card. The system also includes a second display in communication with the second card reader to display the obtained information about the second card. A computer is in communication with the first card reader to process the obtained information and communicate it to the first display. The computer is also in communication with the second card reader to process the obtained information and communicate it to the second display. The computer also resolves any wagers associated with the outcome of the first game and the second game.

32 Claims, 11 Drawing Sheets

(56) References Cited

U.S. PATENT DOCUMENTS

| | | | |
|---|---|---|---|
| 7,407,438 B2* | 8/2008 | Schubert et al. | 463/22 |
| 7,717,427 B2* | 5/2010 | Grauzer et al. | 273/149 R |
| 8,016,665 B2* | 9/2011 | Gururajan et al. | 463/24 |
| 8,021,231 B2* | 9/2011 | Walker et al. | 463/29 |
| 8,142,271 B2* | 3/2012 | Kuhn et al. | 463/13 |
| 8,142,283 B2* | 3/2012 | Lutnick et al. | 463/29 |
| 8,182,326 B2* | 5/2012 | Speer et al. | 463/16 |
| 8,251,802 B2* | 8/2012 | Snow | 463/25 |
| 8,262,475 B2* | 9/2012 | Snow et al. | 463/31 |
| 8,337,296 B2* | 12/2012 | Grauzer et al. | 463/29 |
| 8,444,148 B1* | 5/2013 | Tseng | 273/149 R |
| 2003/0064798 A1* | 4/2003 | Grauzer et al. | 463/29 |
| 2005/0051955 A1* | 3/2005 | Schubert et al. | 273/149 R |
| 2005/0062227 A1* | 3/2005 | Grauzer et al. | 273/149 R |
| 2009/0189351 A1* | 7/2009 | Baerlocher et al. | 273/309 |
| 2010/0001467 A1* | 1/2010 | Behrendsen et al. | 273/292 |
| 2011/0130185 A1* | 6/2011 | Walker | 463/13 |
| 2013/0237302 A1* | 9/2013 | Frazin | 463/13 |

* cited by examiner

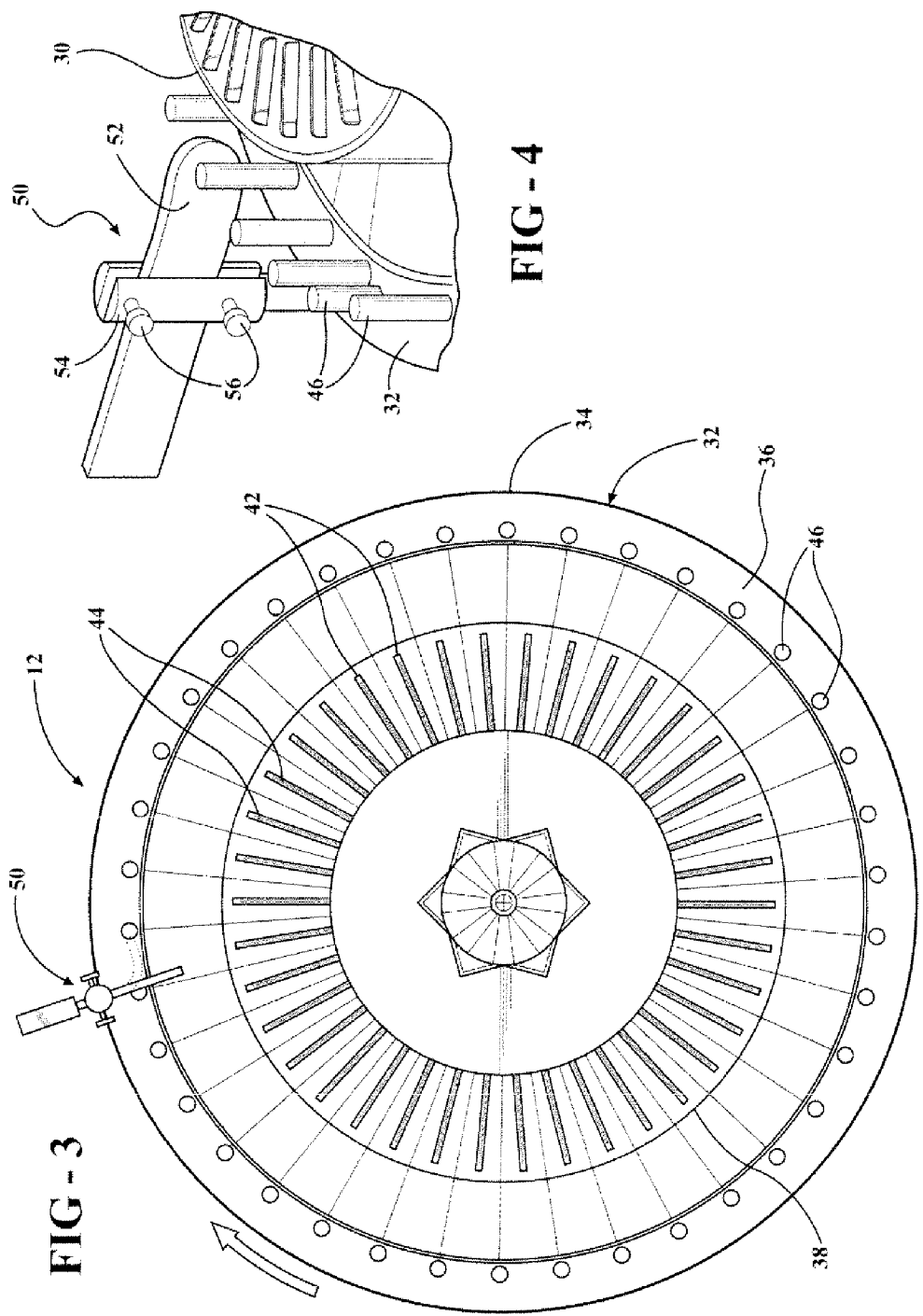

FIG - 10

TURBO CARD TABLE GAME WITH RFID CARD IDENTIFIER

CROSS-REFERENCE TO RELATED APPLICATIONS

The present application claims priority to U.S. Provisional Patent Application Ser. No. 61/565,057, entitled "Turbo Card Table Game and RFID Card and Tip Button", and filed on Nov. 30, 2011, which disclosure is hereby incorporated by reference as though set forth fully herein.

TECHNICAL FIELD

The present disclosure relates generally to a machine for randomly selecting a single card from among a set of cards in a game of chance, which minimizes the need for operator input. More particularly, the present invention relates to a system involving a plurality of devices that each randomly selects a single card from among a set of cards for multiple games of chance that minimizes the costs normally associated with live Dealers.

BACKGROUND OF THE INVENTION

Games of chance are well known activities whose outcomes are strongly influenced by randomizing devices, and upon which contestants may or may not wager money as they forecast outcomes. Common randomizing devices include dice, spinning tops, playing cards, roulette wheels, prize wheels, and numbered balls drawn from containers. Games of chance have been played throughout all of human history, and are considered to be a popular pastime by many. Players of games of chance are attracted to new and exciting methods of game play, as well as new and exciting randomizing devices. For this reason, the gaming industry is continuously developing new games, and new randomizing devices to maintain player interest and attract new players.

Games of chance that include money wagers are typically regulated by governing authorities. These governing authorities enforce laws and regulations that are enacted to curtail certain kinds of games, as well as certain kinds of randomizing devices. For example, in some jurisdictions, the use of dice or roulette wheels to resolve a game outcome, i.e., as the randomizing device, have been curtailed while other randomizing devices such as playing cards are permitted. More frequently, playing cards enjoy a less restrictive use in games of chance played for money, whereas dice and roulette wheel randomizing devices are subject to greater restrictions.

Additionally, table games managers are continually looking for ways to improve the efficiency of their Dealers in connection with all games, thereby reducing labor costs in the long run. Unlike slot managers, who do not have to worry about employee mistakes that cost the casino money (known as bleed), table games managers face these issues on a daily basis. As casinos gets busier and the tables get fuller, the decisions per hour can decrease dramatically and the potential for bleed increases significantly.

Therefore, there is a desire within the gaming industry to develop new and interesting methods of game play and randomizing devices which utilize playing cards in unique and interesting ways, suited to fast-paced, high-volume activity and which minimize the opportunity for bleed.

SUMMARY OF THE INVENTION

It is therefore an advantage of the present disclosure to provide a table game system that can improve the efficiency of the casino dealers.

It is another advantage of the present disclosure to provide a table game system that can reduce the labor costs attributable to the operation of the game.

It is still another advantage of the present disclosure to provide a table game system that can minimize dealer errors and bleed.

It is yet another advantage of the present disclosure to provide a table game system that can increase security measures.

It is a further advantage of the present disclosure to provide a table game system that can provide increased player entertainment and enjoyment.

In accordance with the above and the other advantages of the present disclosure, an improved table game system is provided. The table game system includes a first shuffling machine for randomly selecting a first card from among a first defined set of cards. The first shuffling machine is configured to determine an outcome for a first game of chance. The system also includes a second shuffling machine for randomly selecting a second card from among a second defined set of cards. The second shuffling machine is configured to determine an outcome for a second game of chance. A first card reader is associated with the first shuffling machine for communicating with the selected card to obtain relevant information thereabout. A second card reader is associated with the second shuffling machine for communicating with the selected card to obtain information thereabout. The system includes a first display in communication with the first card reader to display the obtained information about the first card. The system also includes a second display in communication with the second card reader to display the obtained information about the second card. A computer is in communication with the first card reader to process the obtained information and communicate it to the first display. The computer is also in communication with the second card reader to process the obtained information and communicate it to the second display. The computer also resolves any wagers associated with the outcome of the first game and the second game.

BRIEF DESCRIPTION OF THE DRAWINGS

These and other features and advantages of the present invention will become more readily appreciated when considered in connection with the following detailed description and appended drawings wherein:

FIG. 3 is a top plan view of a shuffling machine in accordance with an aspect of the disclosure;

FIG. 4 is an enlarged view of the detent mechanism as depicted by the circumscribed region in FIG. 3;

FIG. 10 is a schematic illustration of the front sides of a set of playing cards in accordance with an aspect of the disclosure;

DETAILED DESCRIPTION OF THE PREFERRED EMBODIMENT

The present disclosure relates to a table game system 10 including two separate shuffling machines 12, 14. The utilization of two shuffling machines 12, 14 allows the system to operate as a double apparatus game, such as a roulette game, where a single dealer can operate 2 roulette games (distinguished from one another in the Figures as "A" and "B" respectively) at the same time with zero Dealer errors, high game security integrity, large numbers of decisions per hour and requiring almost no management supervision. According to an aspect, trained Dealers may be replaced with relatively unskilled operators because they are not required to make game decisions.

Figure 1:
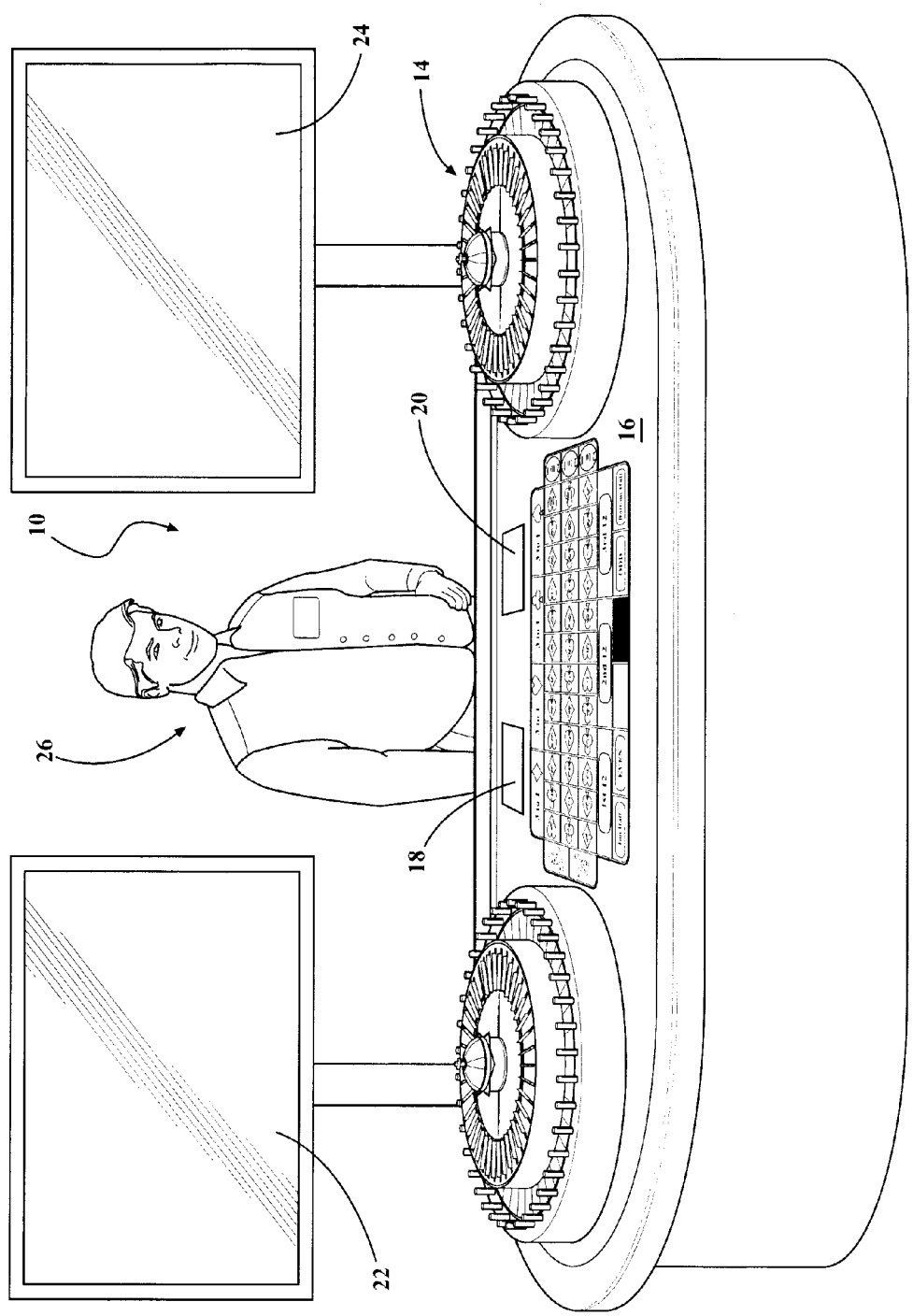
FIG. 1 is a perspective view of a table game system, including a plurality of shuffling machines, according to an aspect of the disclosure.
Figure 2:
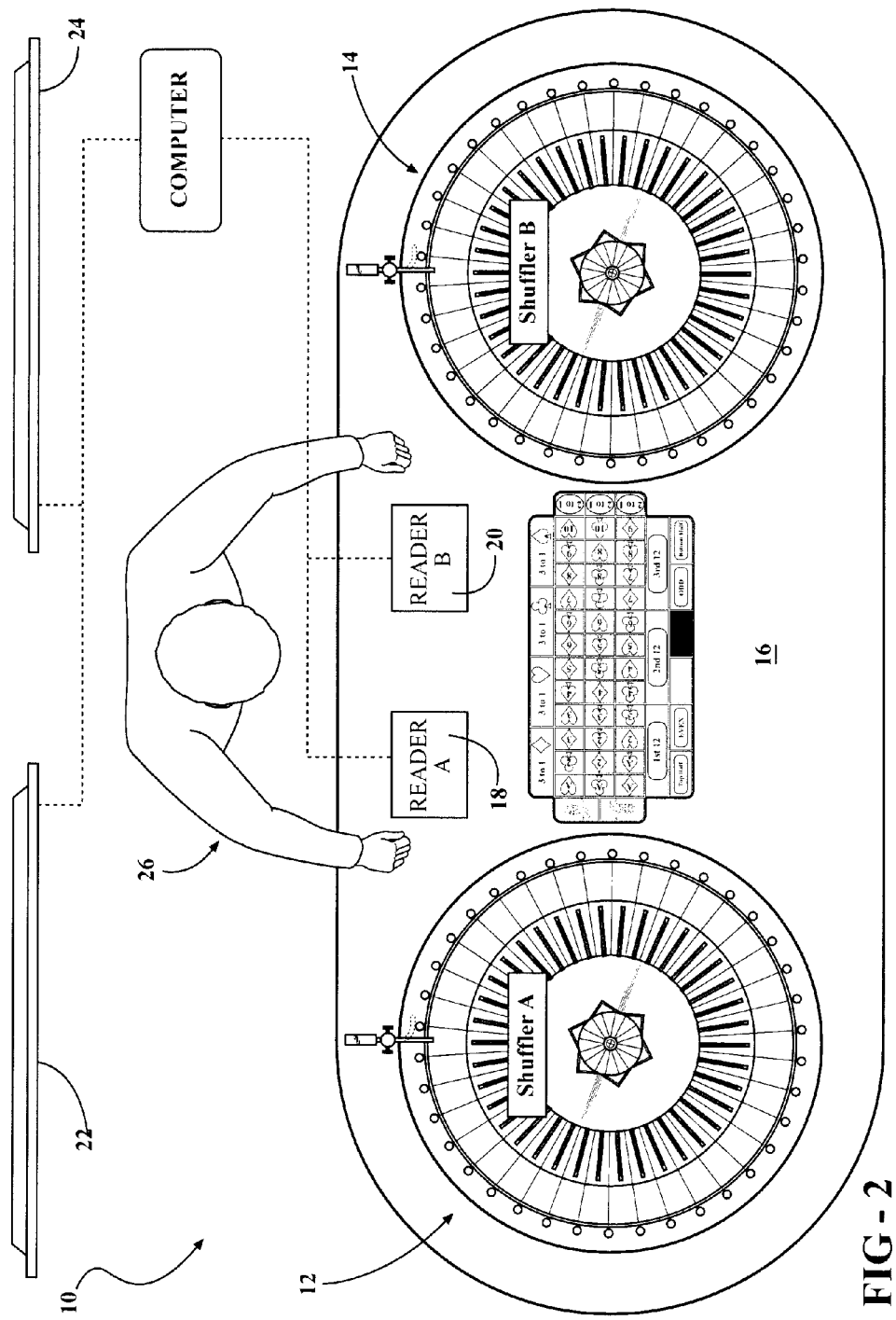
FIG. 2 is a top schematic view of the table game system having a plurality of shuffling machines of FIG. 1.

According to an aspect, as shown in FIGS. 1 and 2, the pair of shuffler machines 12, 14 sit on a table 16 and can be spaced generally an arms-spread distance apart. The spacing of the shufflers is advantageous so that a single dealer/operator can simultaneously attend to both shuffler machines 12, 14. It will be appreciated that the shuffler machines 12, 14 may be spaced different distances apart and be disposed in various different arrangements. According to an aspect, the configuration of the table game system 10 allows for the simultaneous play of two games of roulette. According to another aspect, the system 10 includes no physical game layout, no chips and is operable with only one dealer/operator. Alternatively, each shuffler machine 12, 14 could allow for the play of a different game such that two different games could be manned by a single dealer.

According to a further aspect, the table game system 10 includes a pair of card readers 18, 20 and a pair of display screens 22, 24. According to an aspect, the card readers 18, 20 may be RFID card readers, as discussed in more detail below. Alternatively, other suitable electronic scanning devices may be used to input the selected card from each shuffler into a suitably programmed electronic game server configured to execute the game being played by each respective shuffler machine A and B. The results of the game and/or other information may be displayed on the display screens 22, 24, which are visible to the players. The table game system 10 may also include a live Dealer 26. According to an aspect, one or more game layouts could be disposed on the table 16. According to an aspect, betting terminals are located at or adjacent to table 16 and are associated with the shuffling machines 12, 14 for use by the Dealer to control the game.

The shuffling machines 12, 14 are now discussed with reference to FIG. 3. According to an aspect, the first shuffling machine 12 and the second shuffling machine 14 have the same configuration and thus only one will be described as that description applies equally to both. The shuffler machine 12 randomly selects a single card from among a set of cards and includes a stationary base 30 which is effective to establish a generally vertical central axis A. In accordance with one aspect of the disclosure, the base 30 is shown as a squat, generally cylindrical member. However, this configuration can be varied as desired. A turntable 32 is movably supported above the base 30 for free rotation within a generally horizontal plane about the central axis A. The turntable 32 has a generally circular outer periphery 34, and in this embodiment, is configured with multiple levels forming a hat-like construction. More specifically, an outer rim section 36 is circumscribed by the outer periphery 34 and rests directly above the stationary base 30. An elevated stage section 38 is centrally located therein. A decorative crown piece 40 may be affixed centrally within the stage section 38 for purely aesthetic purposes.

According to an aspect, the stage section 38 of the turntable 32 can include a plurality of trays 42. In one example, the defined plurality of trays 42 may consist of exactly thirty-eight trays. Depending upon the game of chance to be played, however, the defined plurality of trays 42 can be varied to include more than or less than the exemplary thirty-eight trays illustrated here. The trays 42 can be equally circumferentially spaced apart one from another about the central axis A. In other words, in this exemplary aspect where thirty-eight trays 42 are provided, each tray occupies a sector of approximately 9.47 degrees. If the number of trays 42 were decreased to thirty-six, for example, each tray 42 would occupy a sector of exactly 10 degrees, and so forth. The trays 42 may, as shown in the FIGs., comprise narrow slots arranged along radials extending from the central axis A. Each slot is sized, shaped and oriented so as to hold a single playing card 44 in a vertically upstanding orientation. It will be appreciated that the configuration of the slots may vary. Also, the cards can be retained in a variety of other suitable ways.

Figure 10:
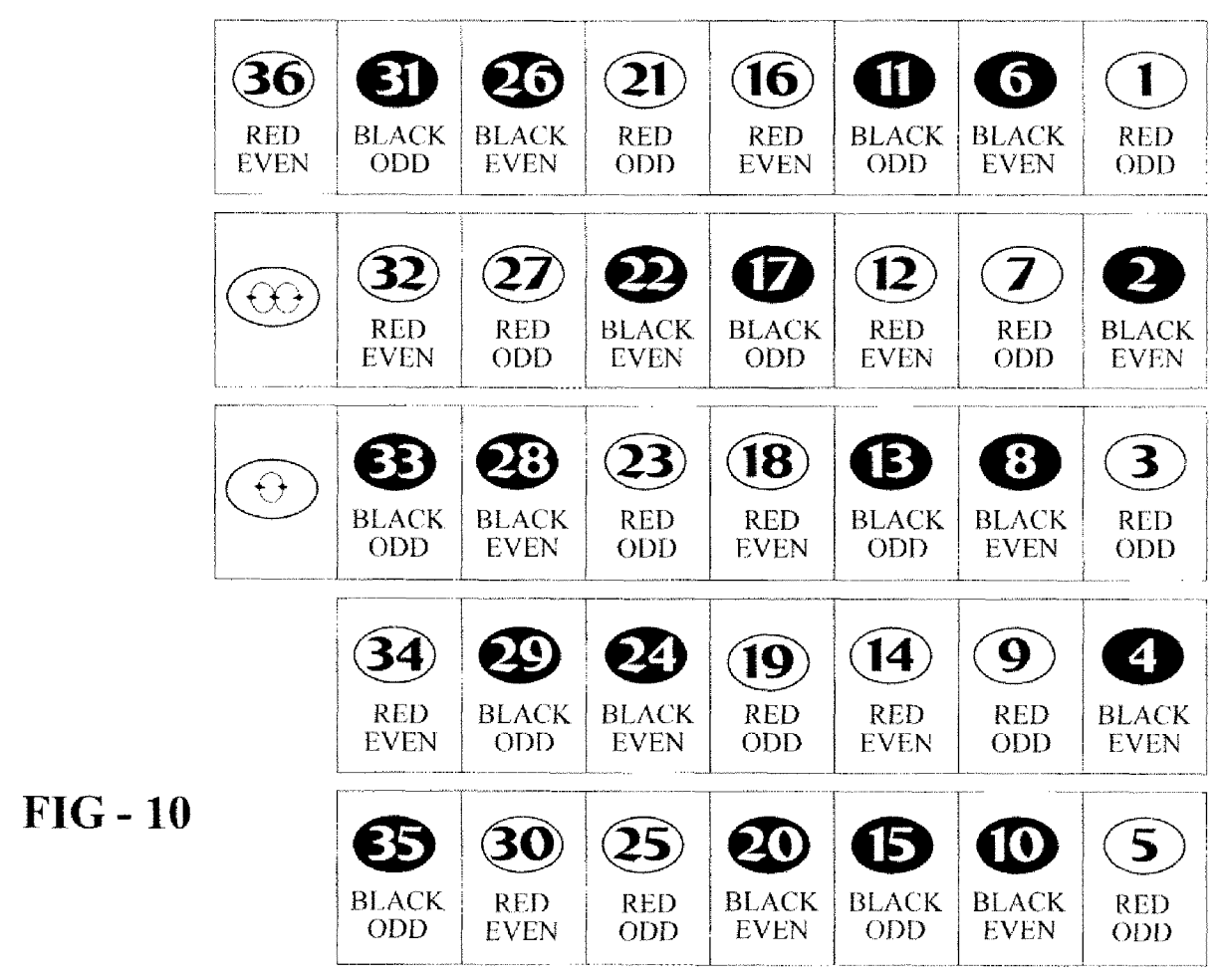
Figure 11:
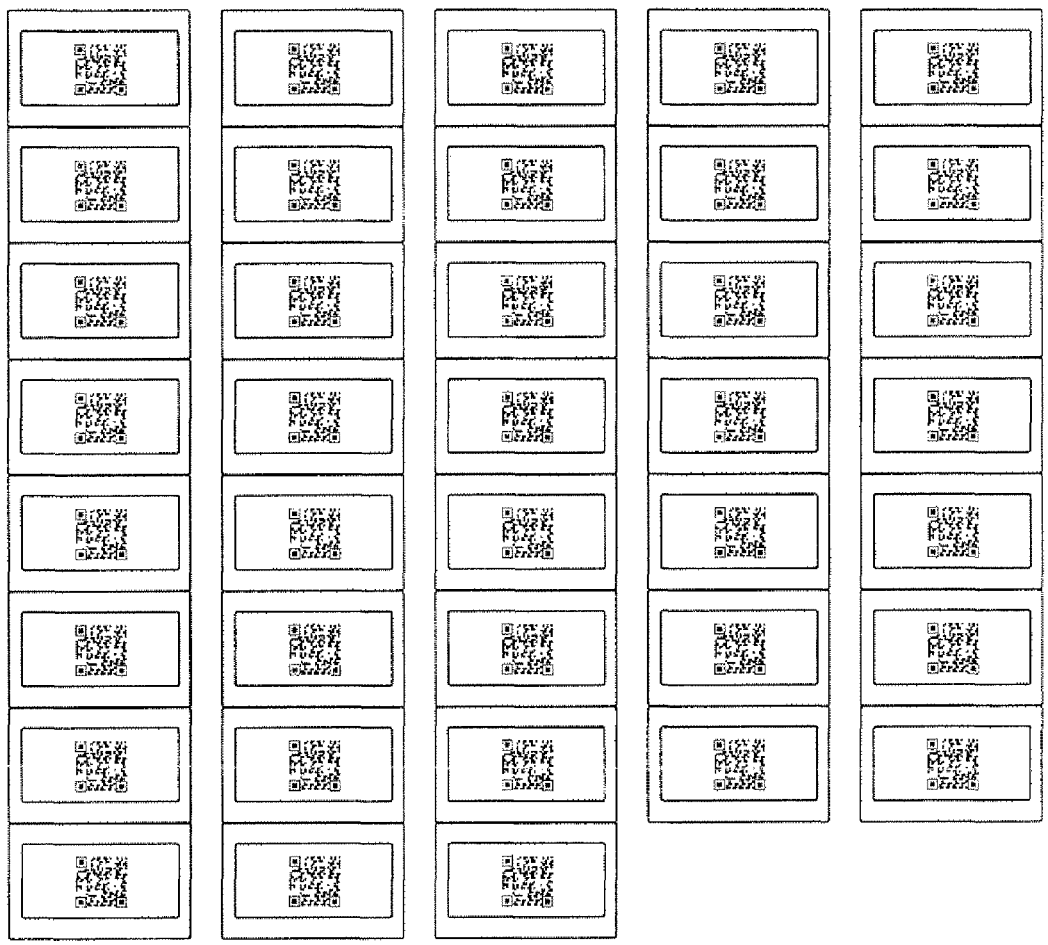
FIG. 11 is a schematic illustration of the back sides of the set of playing cards of FIG. 10.
Figure 12:
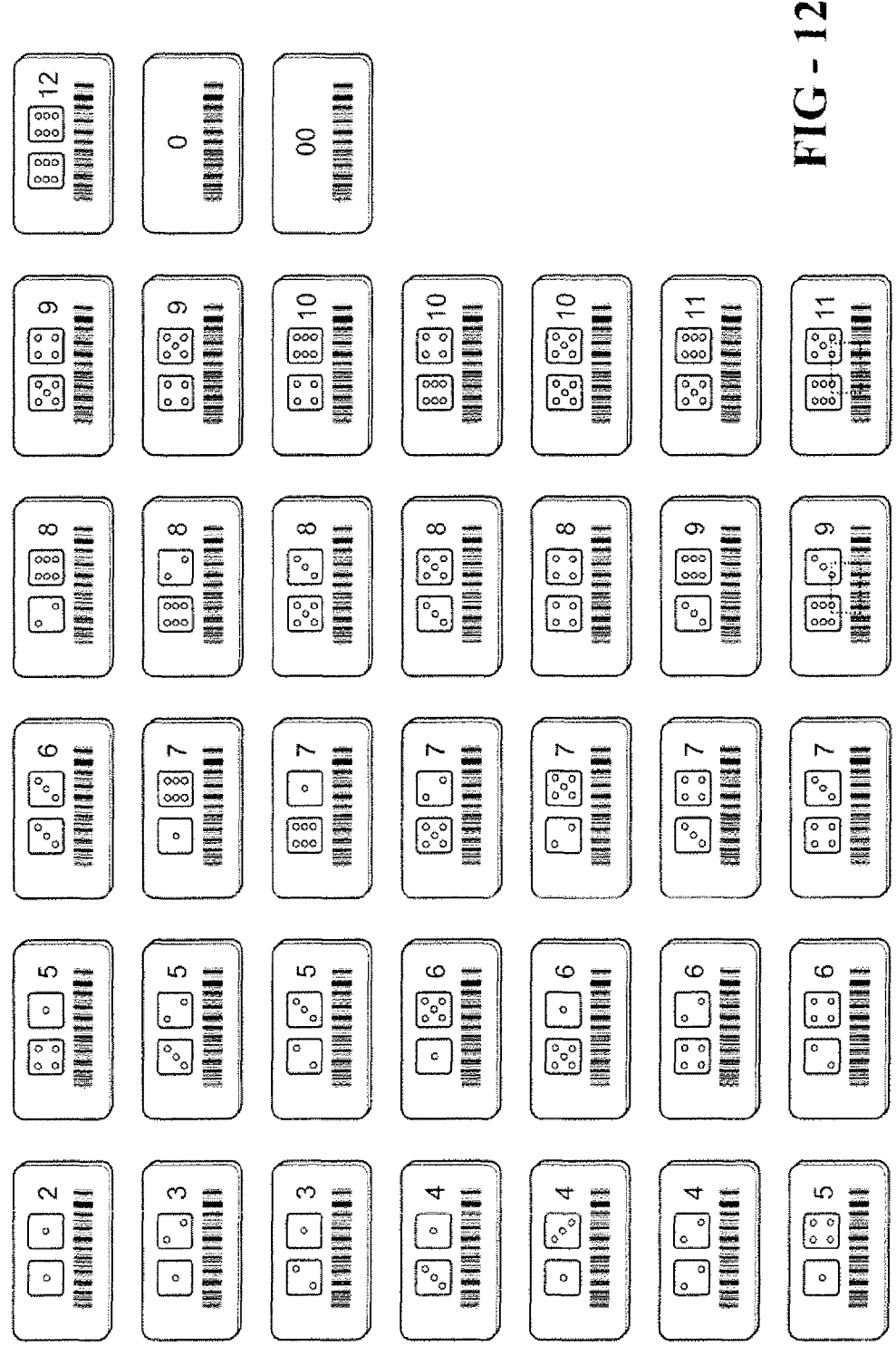
FIG. 12 is a schematic illustration of a set of playing cards in accordance with another aspect of the disclosure.

The card 44 may be dimensionally similar to those used for playing card games like poker, blackjack and the like. Instead of the traditional rectangular configuration, the cards 44 may be shaped in other interesting or effective geometries. In accordance with one example, a set of cards 44 is equal in number to the defined plurality of trays 42. Thus, in keeping with the previously proposed example of thirty-eight trays, a set of cards would consist of thirty-eight distinct cards. FIGS. 7, and 9-11 illustrate exemplary cards according to aspects where the game of chance is roulette. FIG. 12 illustrates another aspect, wherein thirty-eight cards 44, which comprise a distinct set of cards, are suitable for the game of craps. It will be appreciated that the cards may be configured for other games and more or less cards may be employed.

According to an aspect, the trays 42 are arranged so as to hold each card 44 so that its long edges are oriented horizontally, and its short edges are oriented vertically. The depth of each slot in the trays 42 is less than the narrow width of each card 44, so that a noticeable, protruding portion of each card 44 extends above the stage section 38 of the turntable 32. This protruding portion may allow the dealer or operator of a game of chance using the shuffling machine 12 to easily remove a card 44 from its tray 42. Thus, each card 44 is loosely contained in its respective tray 42 without the use of fastening devices, spring clips, or any other fixation medium. Other configurations may be employed as desired.

The rim section 36 of the turntable 32 may be provided with a plurality of dividers 46. The plurality of dividers 46 are equal in number to the defined plurality of trays 42. Thus, in the exemplary embodiment where thirty-eight trays are provided, the number of dividers 46 is also thirty-eight. The dividers 46, like the trays 42, are also spaced one from another in equal circumferentially-spaced increments about the central axis A. Thus, if the trays 42 are spaced one from another 9.47 degrees, the dividers 48 are likewise spaced one from another 9.47 degrees. Accordingly, the space between each divider 46, as measured from center-line to center-line, occupies a sector equal to 9.47 degrees, or whatever accurate measure is achieved when the number 360 is divided by the number of dividers 46. Preferably, although by no means necessarily, the dividers 46 are oriented so as to perfectly bisect the angular sector between each adjacent tray 42. Put another way, a radial extending from each divider 46 to the central axis A is preferably, but not necessarily, offset from the center-line of each adjacent tray 42 by an angular measure equal to the total number of trays 42 divided by 720. In this manner, the space or gap between each divider 46 may be exclusively associated with one specific tray 42. It will be appreciated that other arrangements may be employed.

As best show in FIG. 4, a detent 50 is fixed relative to the base 30 and operatively interacts with the dividers 46. The detent 50 functions to apply a pulsating resistance to the free rotation of the turntable 32 and thereby progressively slow the turntable 32 to a stopped condition relative to the base 30. According to an aspect, the detent 50 comprises a resiliently flexible tongue 52 supported in a retractable clamping holder 54 so that the tongue 52 can be withdrawn from the movement path of the dividers 46. In this example, the dividers 46 comprise upstanding pegs which are fixed to the rim section 36 of the turntable 32 at exactly equally radially spaced measurements from the central axis A. It will be appreciated that the divider can take on a variety of different configurations. Thus, as the turntable 32 is rotated in the direction of the arrow in FIG. 3, the tongue-like detent is moved to a position that interferes with the paths of the dividers 46. When spun forcefully, the angular momentum of the turntable 32 is sufficient to deflect the detent 50 out of the way in a flipper-like fashion typical of prize wheel type randomizing devices known in the prior art. The tongue 52 of the detent 50 may be made of a felt-like material, or other suitable material. Each sequential impact and deflection of the detent 50 caused by the rotating dividers 46 results in a pulsating resistance which slows the turntable 32 and eventually brings it to a complete stop.

The clamping holder 54 is provided with clamping screws 56 used to tighten or loosen the clamping force upon the detent 50. Preferably, the clamping force is set so that an operator of the card shuffling machine 12 can manually withdraw the detent 50 out of the path of the rotating dividers 46, thereby allowing the turntable 32 to freewheel. When the detent 50 is returned to its position within the path of the moving dividers 46, the detent 50 is operative to frictionally encounter the dividers 46, with each frictional encounter retarding the spin of the turntable 32 until there are enough such encounters to stop the turntable 32. However, those with skill in the art will readily appreciate that many alternative detent type mechanisms, both mechanical and electromagnetic, may be employed to achieve substantially similar results from that of the example just described.

According to an aspect, the card shuffling machine 12 may also include some type of pointing device, which is fixed relative to the base 30, for indicating one of the pluralities of trays 42 when the turntable 32 comes to rest. In accordance with this aspect, the pointer is integral with the detent 50 such that when the turntable 32 comes to rest, it will determine which card 44 is to be selected for the purpose of determining game outcome. Alternatively, a separate and distinct pointer may be used, spaced from the detent 50, to indicate one of the plurality of trays 42 when the turntable 32 stops rotating.

Figure 5:
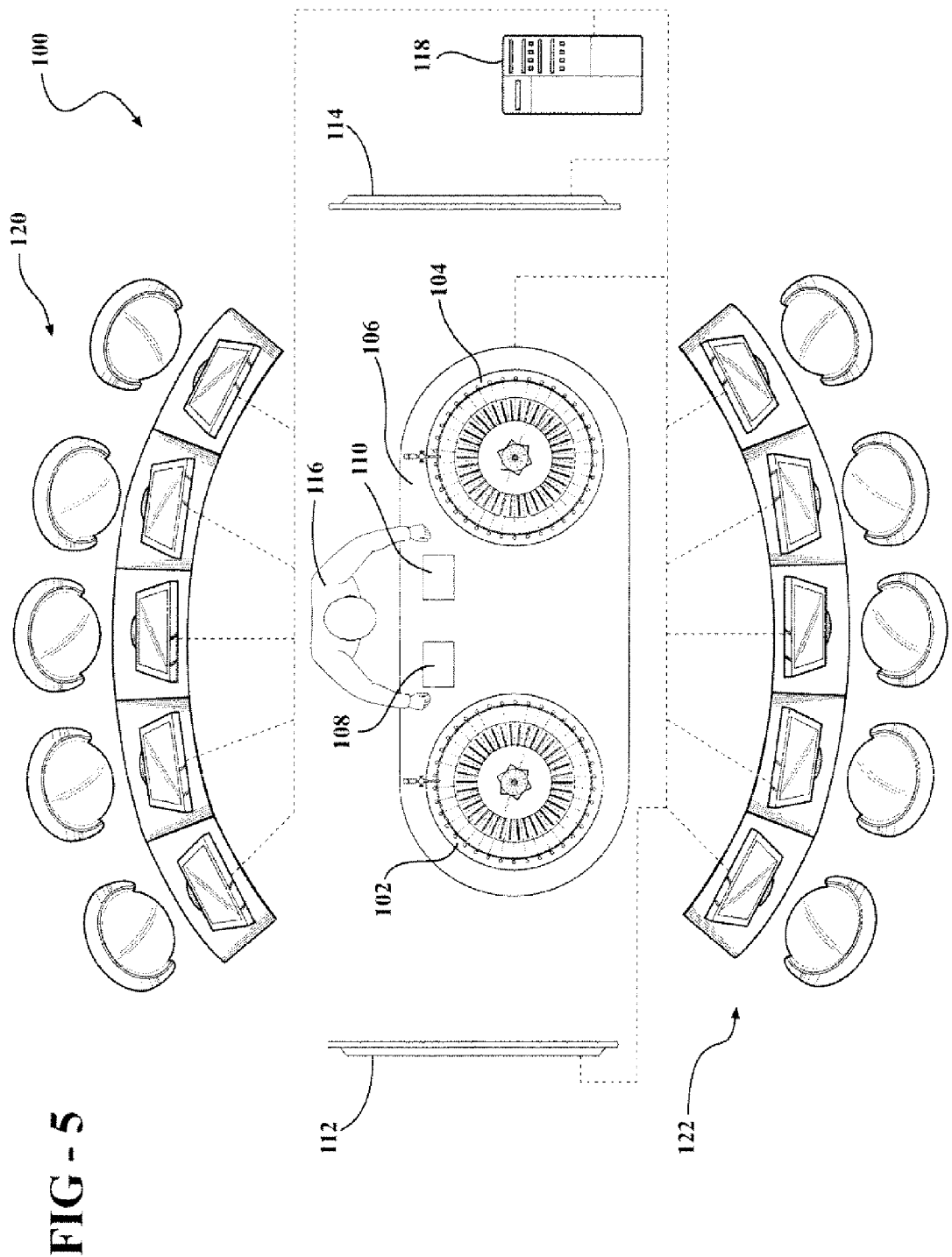
FIG. 5 is schematic view of a table game system, including a plurality of player positions and associated screens, in accordance with another aspect of the disclosure.

FIG. 5 illustrates a table game system 100 in accordance with another aspect of the present disclosure. As shown, the table game system 100 includes a pair of shuffling machines 102, 104 disposed on a table 106. The pair of shuffling machines 102, 104 can each select a single card from a full set of cards. The system 100 also includes a pair of card readers 108, 110 and a pair of display screens 112, 114. According to an aspect, a Dealer 116 is also present. The system 100 also can include a computer 118. Additionally, the system 100 can include a first group of player terminals 120 and a second group of player terminals 122. Each of the groups of player terminals 120, 122 can include a plurality of individual terminals 124. According to an aspect, players stationed at the respective electronic betting terminals 124 may choose to play either or both games associated with the shuffling machines 102, 104. According to another aspect, the players may switch back and forth between playing first from the Shuffler A 102 and then next from Shuffler B 104, and back again, or may play both concurrently as desired. According to an aspect, the players do not need to alert the dealer/operator which game they are playing at any given moment, as the electronic gaming terminal keeps track of this information—including the resolution of wagers placed.

In operation, a card that is selected by the shuffling machine 102 will be read by the card reader 108. The information read from the selected card will be transmitted by the card reader 108 to the computer 118 for processing and also will be displayed on the display screen 112. The players participating in the game of chance will be watching and interacting with the game from the first group of player terminals 120 and/or the second group of player terminals 122. The players can place their bets as well as receive their winnings at the first group of player terminals 120 and/or the second group player terminals 124.

Similarly, a card that is selected by the shuffling machine 104 can be read by the card reader 110. The information read from the selected card can be transmitted by the card reader 110 to the computer 118 for processing and also may be displayed on the display screen 114. The players participating in the game of chance may watch and interact with the game from each of the first group of player terminals 120 and/or the second group player terminals 124. The players can place their bets as well as receive their winnings at the first group of player terminals 120 and/or the second group player terminals 124. The ability to operate a double shuffler with a single operator provides significant advantages over prior systems that only play a single game at a time.

Figure 6:
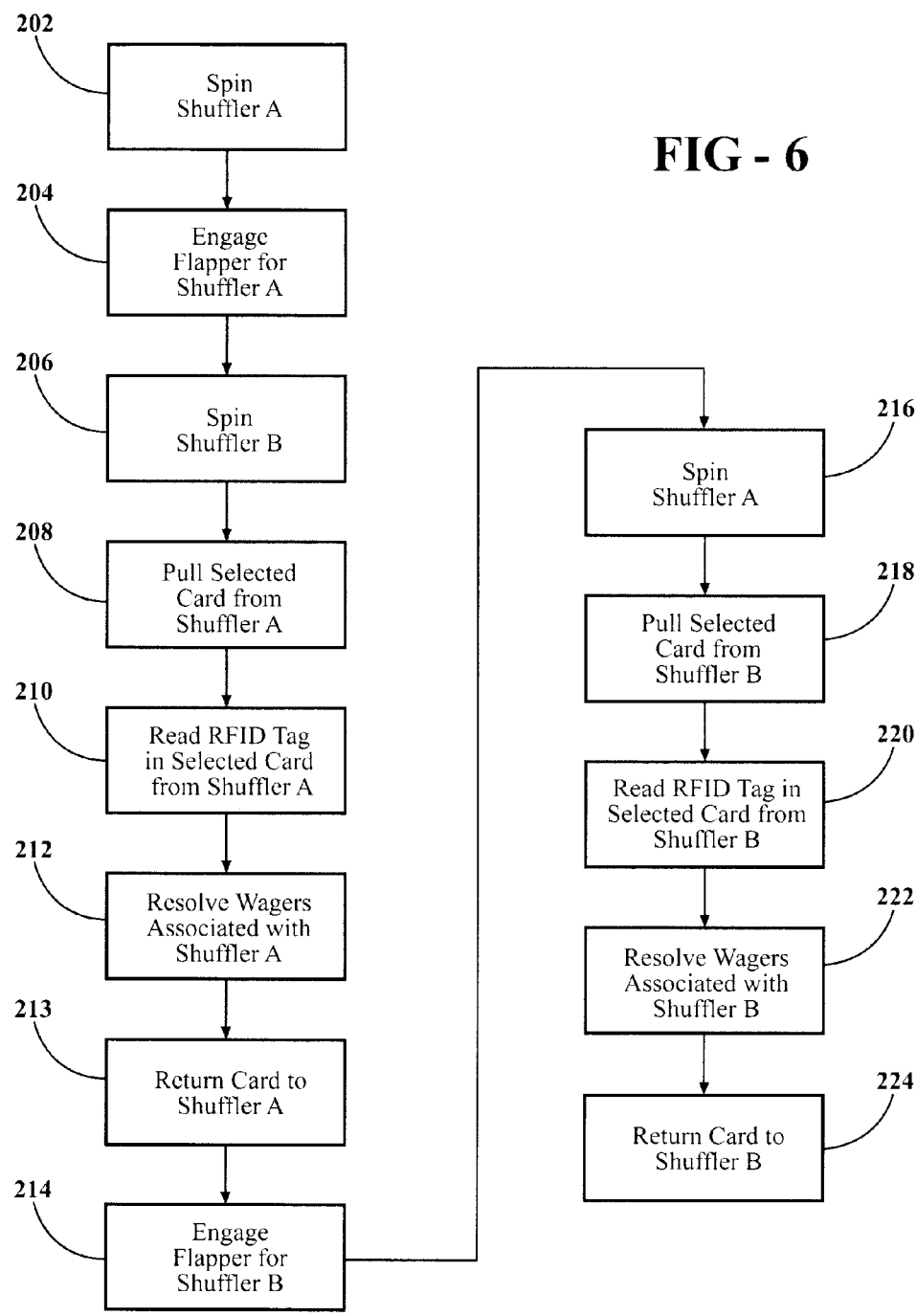
FIG. 6 is a method of operating of a game of chance in accordance with an aspect of the disclosure.

A simplified flow chart illustrating the operation of the system is depicted in FIG. 6. As shown, according to an aspect, the first step of the method is to spin shuffler A, as generally depicted by reference number 200. Next, the flapper of the detent may be engaged such that it begins to slow the turntable of shuffler A, as designated by reference number 202. Then, at step 206, shuffler B 104 is spun. The selected card can then be pulled from shuffler A, such as by the Dealer as reflected at step 208. The RFID tag of the selected card can be read by the card reader, as indicated by reference number 210. All wagers associated with shuffler A can then be resolved automatically, as indicated by reference number 212. The selected card is then returned to shuffler A as generally represented by reference number 213. The flapper of the detent of shuffler B may then be engaged at step 214 so that the turntable of shuffler B begins to slow. Shuffler A may then be spun again, as designated by reference number 216. Then, the selected card can be pulled from shuffler B, as indicated by reference number 218. At step 220, the RFID tag of the selected card from shuffler B may then be read by the second card reader. The wagers associated with shuffler B are then resolved automatically, as generally indicated by reference number 222. The selected card is then returned to shuffler B as generally represented by reference number 224.

Figure 7:
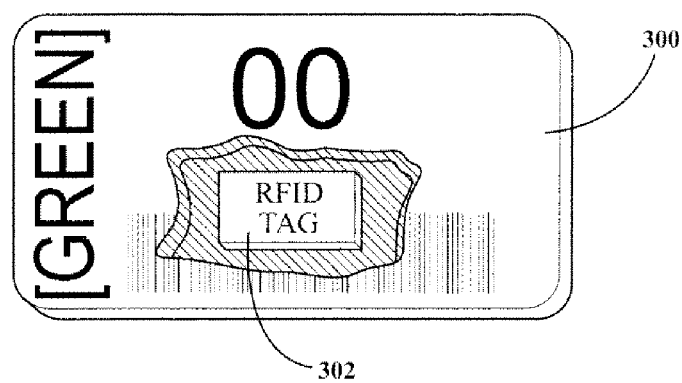
FIG. 7 is a schematic illustration of an exemplary playing card in accordance with an aspect of the disclosure.

FIG. 7 illustrates a card 300 bearing an indicia related to a decision for a game of chance. This exemplary card 300 reflects one of the numbers or results associated with the game of roulette. As shown, the card 300 bears indicia for the number "00" and the color green. According to an aspect, the card 300 also includes an RFID tag 302 associated therewith. According to an aspect, the RFID tag can be embedded in the card 300. As will be understood, the RFID tag 302 contains the information about the card indicia, i.e., color and number thereon.

Figure 8:
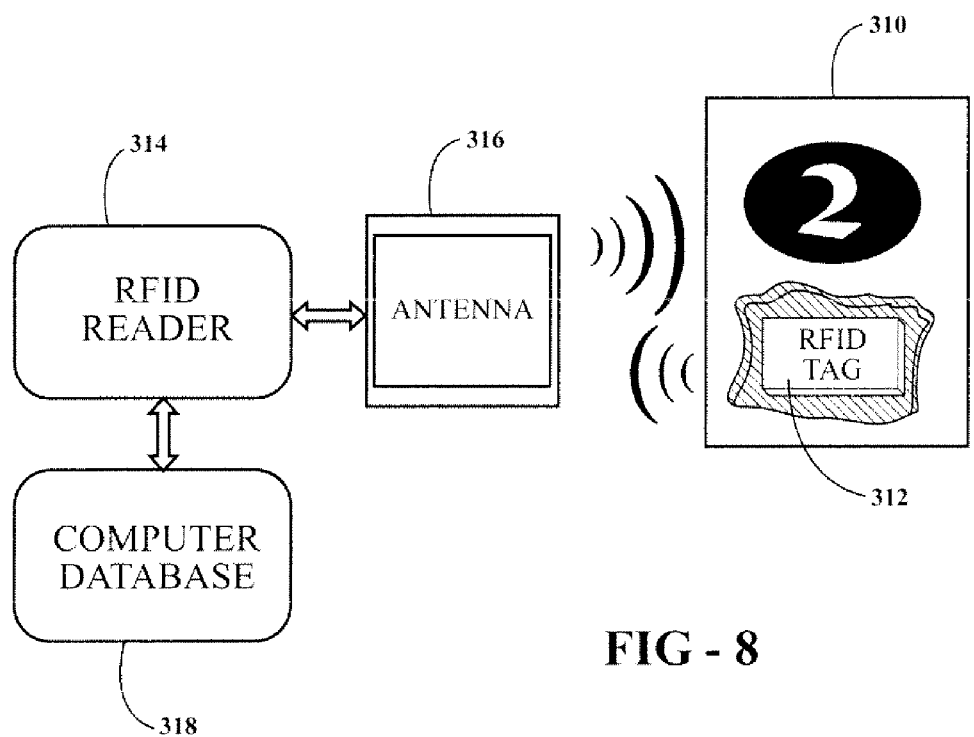
FIG. 8 is a schematic diagram illustrating a method for identifying a specific playing card in accordance with an aspect of the disclosure.

FIG. 8 schematically illustrates the steps of reading a card 310 according to an aspect of the disclosure. As shown, the card 310 bears indicia related to the game of roulette, specifically the number 2 and the color black. An RFID tag 312 associated therewith may have information stored thereon. When the card 310 is brought into proximity with an RFID card reader 314, which includes a wireless antenna 316 to communicate with the RFID tag 312, the RFID card reader 314 reads the information about the card that is stored on the RFID tag 312. The information is then transmitted to a computer database 318 so that it can be utilized to settle wagers and display it on the monitors and terminals.

Figure 9:
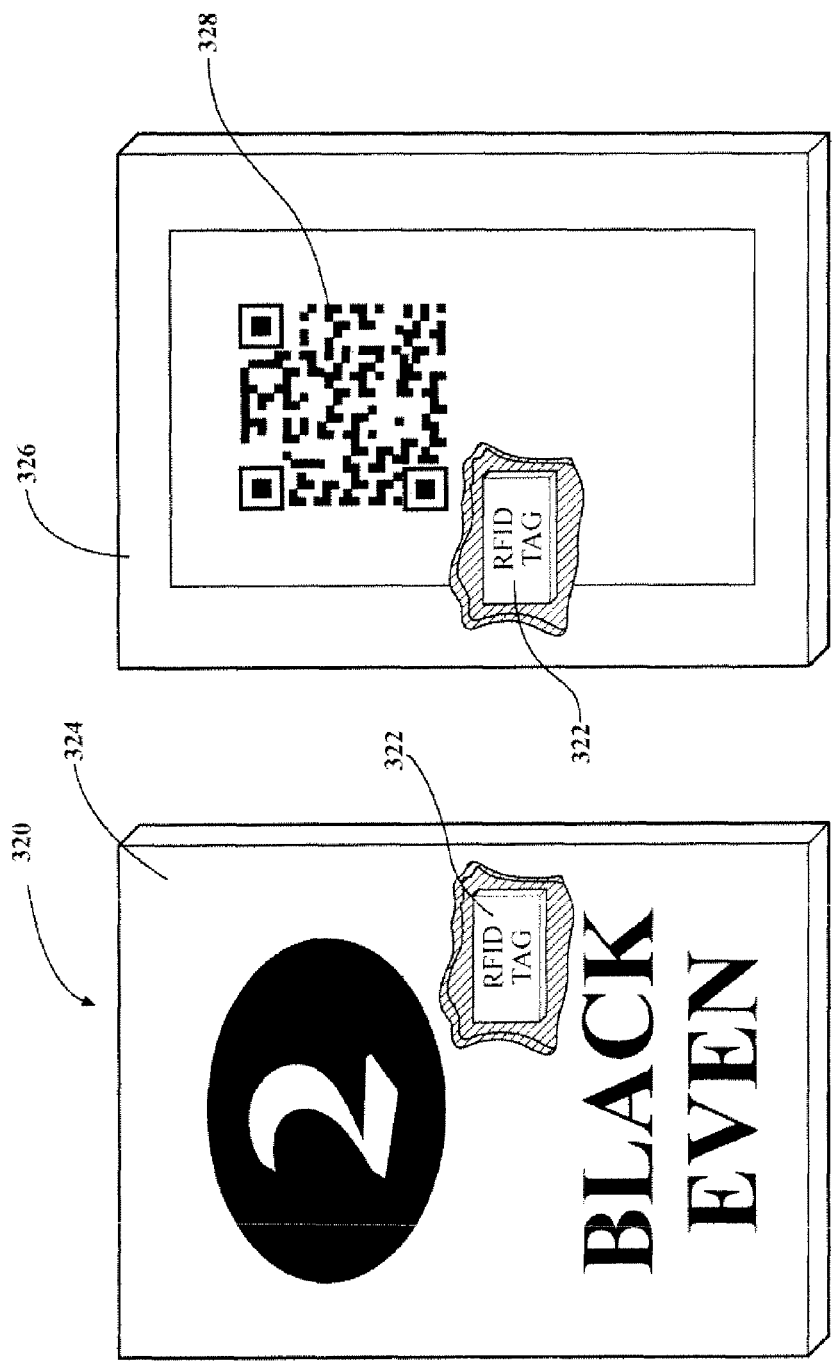
FIG. 9 is a schematic diagram of another exemplary playing card in accordance with an aspect of the disclosure.

FIG. 9 illustrates another exemplary card 320 in accordance with the game of roulette. As shown, the card 320 also bears indicia reflecting a number and a color which are associated with the game outcome. The card 320 has a front side 324 that contains the card indicia and a back side 326. The card 320 can also include an RFID tag 322 embedded therein, which contains the indicia from the card 320 stored thereon for reading by an RFID card reader. According to another aspect, the card 320 may alternatively have a bar code 328 printed on the back side 326 of the card, which also contains the information about the card indicia. According to this aspect, the card reader would have capabilities to read information from the bar code 328 and send it to an associated computer.

As discussed previously, according to an aspect, almost any of the known games of chance can be played using the shuffling machines of the disclosed system, so long as the number of cards and the number of their represented indicia result in a probability of decision which is equivalent to the traditionally played game. For example, it has been discussed that is possible to play a game of chance which conforms substantially to the traditional rules of roulette using a set of cards bearing indicia substantially as depicted in FIGS. 10-11. Illustrated in FIG. 10 are thirty-six cards that are marked with distinct indicia selected from the group consisting of the whole numbers 1 to 36. Also, in keeping with the traditional rules of roulette, eighteen of the cards may be marked with the color red indicia, while eighteen different cards are marked with the color black indicia. This corresponds to the red and black colors used in traditional roulette. Two additional cards are colored with the green indicia and marked 0 and 00, respectively. When these cards are arranged in the trays of the card shuffling machines, any single one of these cards can be selected from the set of cards, and its particular indicia used to decide the game of chance.

According to another aspect, the card shuffling machines can be used to play a game according to the traditional rules of craps. The randomizing device used in the traditional game of craps consists of a pair of six-sided dice, each side of the dice bearing a dot representative of the whole numbers 1 to 6. Considering the pair of dice together, thirty-six possible combinations can be achieved by the two dice. In accordance with another aspect, as shown in FIG. 12, the set of cards 400 may be marked with indicia representing the whole numbers 2 to 12 in the following combinations: one number 2, two number 3's, three number 4's, four number 5's, five number 6's, six number 7's, five number 8's, four number 9's, three number 10's, two number 11's, and one number 12. These cards may also be imprinted with indicia which pictorially represents all thirty-six available combinations of a pair of six-sided dice. When arranged in a turntable consisting of thirty-six equally spaced trays, complete odds parity with the traditional game of craps can be achieved through use of the subject card shuffling machine. To add variety to the traditional game of craps, one or two additional cards bearing the indicia 0 and 00 can be added. Likewise, other games of chance can be played using the card shuffling machine of this invention as the randomizing device. Such games may include blackjack, war, and many others.

According to an aspect, the cards may be constructed of a hard plastic. The back sides of the cards as shown in FIG. 11 can also include the game logo on the back of the card. The shuffler machines are configured to hold the RFID-enabled hard plastic custom cards shown in FIGS. 7-12. According to an aspect, several advantages can be achieved using these custom cards. First, they provide a huge increase in game security as the cards can be memorized by the computer system one at a time when they are placed into the shuffler. If an unauthorized person tries to insert a card that was not one originally placed in the shuffler, it will not be read therefore it will not communicate with the game server which settles wagers at the terminals. This can eliminate one cheating threat. By using these custom cards, the system can also eliminate the need for the operator to manually input the decision number. Instead, the operator can remove the card from one of the shufflers (A or B) and lay it on the associated reader (A or B). The pre-programmed software running on the linked computer server can display the card # which allows the operator to confirm that these match before proceeding. The information can then be posted on the game terminal and public display and all wagers are settled based on this confirmation. The software will not allow the operator to enter the wrong number. This also eliminates Dealer/Customer collusion which is a major problem on live table games.

Unlike conventional shufflers, the cards may stay in a stationary position while the shuffler moves to create the random card selection. The operator can keep both shufflers moving and move back and forth from one game to the other (as suggested in FIG. 6). According to an aspect, the players can have 2 game layouts available on their game monitors. Instead of A and B, it may be preferable to distinguish the games in other easily identifiable ways, such as by using two different layout colors (Red and Blue for example) to make it simple for the player to see which game is currently in the decision mode. The player can play either of the games or both, based on their desired risk acceptance and the size of their bank role.

In a standard dealer dealt game, as more players join the game, the casino's decisions per hour decreases as it takes the Dealer longer to make the payouts. A full standard Roulette game will play about 39 hands per hour with an experienced dealer. According to an aspect, the disclosed system using the double apparatus game (whether a standard wheel, ball blowers or shufflers are utilized) can generate on average 120 decisions per hour no matter how many players join into the game. This can provide a major increase in potential revenue to the casino. According to an aspect, the disclosed system can accommodate a large number of individual player terminals. By adding a router which provides unlimited connectivity, the number is significantly higher. The current invention also gives the casino unlimited flexibility in floor configuration.

According to an aspect, the advent of the double apparatus game with its huge increase in decisions per hour can allow the casino the ability to reduce the minimum wager a customer must place to be in action. This can enhance the player's entertainment value as they should be able to play for a longer period of time on their fixed bankroll. This added value comes at no cost to the casino and is a built in value to the casino.

The system allows the casino the ability to place wagering terminals in multiple locations in the casino utilizing the same single operator by broadcasting the game using live feeds from the local betting terminals. When the operator touches the "no more bets" option on the local betting terminal screen, a live feed will be broadcasted to the terminals and public displays so that the players can view the dealer removing the card and seeing the number drawn. This will provide the players with a warm and fuzzy feeling that all is on the up and up.

The system can provide significant advantages in that it can give the casino the opportunity to eliminate dealer training, surveillance training, dealer error, casino bleed and reduced supervision while increasing decisions per hour not seen before and at the same time passing on benefits to the players by allowing them to stretch their bankroll by offering smaller minimums and longer potential time on device.

Figure 13:
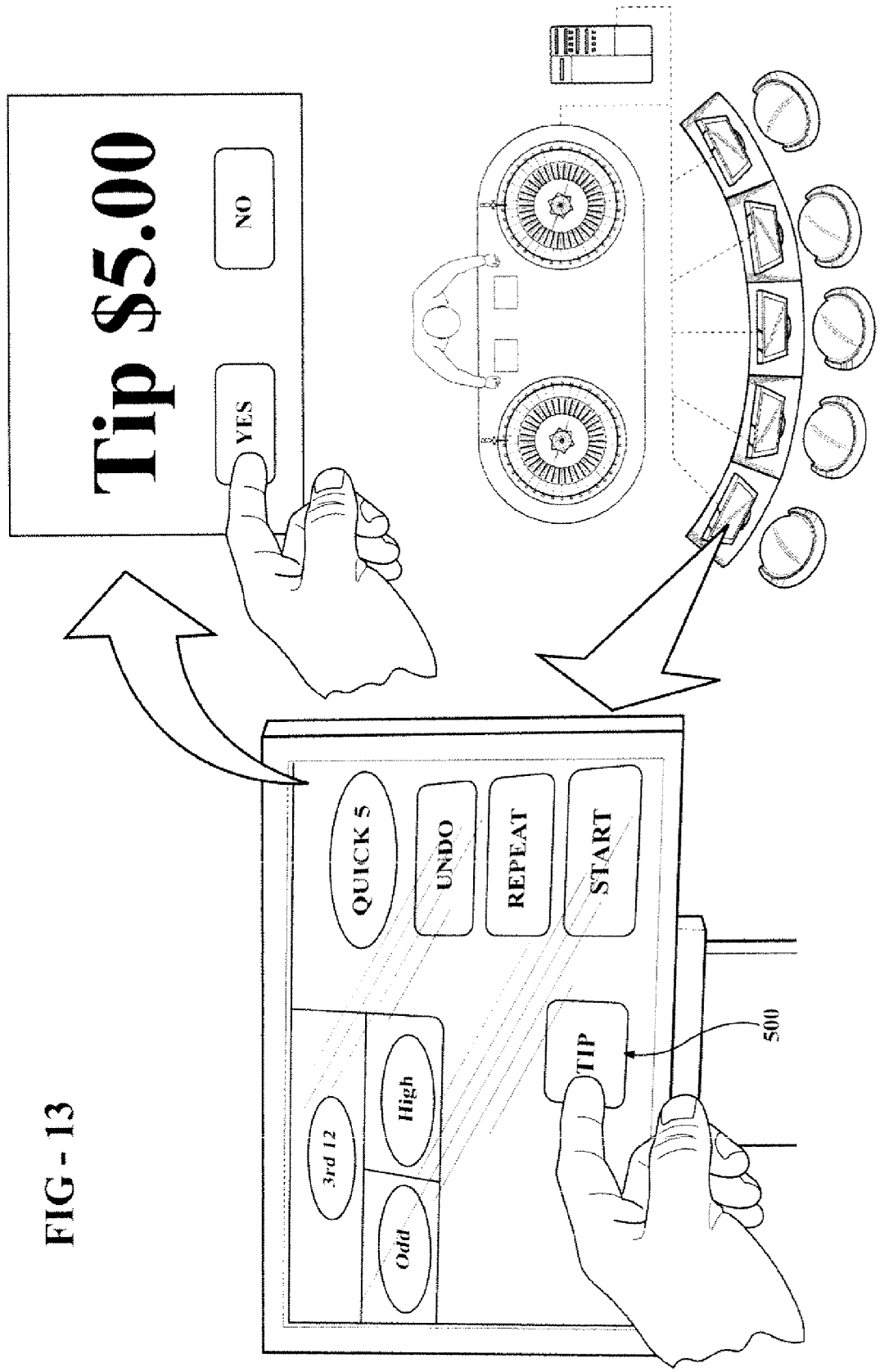
FIG. 13 is a schematic illustration of a game of chance having a tip button in accordance with an aspect of the disclosure.

FIG. 13 illustrates a further enhanced feature that can be used alone or in combination with this present system. Specifically, the player terminals can include a "Tip" button feature 500 on the user interface screen. With this feature, a player can easily and discretely provide the dealer/operator with a gratuity by simply touching the "TIP" icon on their screen. Doing so, according to an aspect, can activate a confirmation screen that the player must address in order to consummate the tip transaction. Such tips are aggregated and remitted to the dealer/operator at a convenient time. The Tip button 500 can be particularly useful in situations where there is a substantial distance between the dealer/operator and the player. In other words, the Tip button 500 can enable players to tip the Dealer/Operator from satellite wagering stations.

According to an aspect, the tip button feature is not limited to the dual wheel shuffler system. In fact, the tip button feature could be incorporated into any electronic game player interface, including for slot machines, electronic table games or any other wagering system to award the dealer or operator. The ability to transfer credits to an individual's account of a pool can help a new game become successful as the employees will help promote the game. The button can be a virtual button on the touch screen (software) or a physical button (hardware).

According to another aspect, the card reading device may be in the form of a laser scanner, that is capable of recognizing the machine readable indicia on the one selected card 44 and then publishing the identity of the indicia upon a video monitor. In an even more sophisticated extension of this concept, a plurality of such video monitors may be provided in the form of computerized consoles. These consoles may be of the touch screen variety commonly known for the casino games of video poker and the like. It is intended that one computerized console would be associated with each individual player of the game of chance. Seats may be arranged directly opposite each computerized console. In this embodiment, a bet selection region is projected on to the computerized consoles which, for the example of a roulette type game, may take the graphical appearance of a traditional roulette table. Players make their forecast of the game outcome by associating a marker on the bet selection region of the computer console. Many such computerized consoles may be operated simultaneously, and each communicates directly, or indirectly, with a digital processor. At the start of each game, each player wagers according to the game rules and makes a forecast on the game outcome. A dealer places the turntable 32 into rotation and, at the appropriate time, engages the detent 50 to progressively slow the turntable 32 to a stop condition. Thereupon, a pointer identifies one tray 42, from which the associated card 44 is withdrawn, i.e., selected. The dealer then passes the one selected card 44 in view of the card reader 42, causing the digital processor to recognize the game decision and resolve each individual player's game via their computerized consoles. In situations where wagers are resolved at each game console, as in ticket in-ticket out (TITO) and other such systems, there is no requirement for the dealer or game operator to handle chips, tokens or cheques. The dealer may also be provided with a graphical user interface (GUI) to be of the touch screen variety. Through such a GUI, the dealer may effectively administer the game and the wagering process.

According to an aspect, electronic posting of the selected card 44 can flow through both a reader board and game processing software to add speed, certainty and enjoyment to the game play. Of course, other card reading formats and card recognition techniques may be employed with, or without, any visible markings on the cards 44. Alternatively, a dealer can manually input the card value, i.e., indicia, manually to the digital processor via the GUI.

The foregoing invention has been described in accordance with the relevant legal standards, thus the description is exemplary rather than limiting in nature. Variations and modifications to the disclosed embodiment may become apparent to those skilled in the art and fall within the scope of the invention. Accordingly the scope of legal protection afforded this invention can only be determined by studying the following claims.

What is claimed is:

1. A table game system, comprising:
    a game surface having a plurality of player positions disposed therearound and a dealer position;
    a first shuffling machine disposed adjacent the dealer position for randomly selecting a first card from among a first defined set of cards, the first shuffling machine configured to determine an outcome for a first game of chance;
    a second shuffling machine disposed adjacent the dealer position for randomly selecting a second card from among a second defined set of cards, the second shuffling machine configured to determine an outcome for a second game of chance;
    a first card reader disposed on the game surface and associated with the first shuffling machine for communicating with the first selected card to obtain indicia information relevant to the outcome of the second game of chance;
    a second card reader disposed on the game surface and associated with the second shuffling machine for communicating with the second selected card to obtain indicia information relevant to the outcome of the second game of chance;
    a first display device in communication with the first card reader and configured to display indicia of the first selected card to any players located at the plurality of playing positions disposed around the game surface;
    a second display device in communication with the second card reader and configured to display indicia of the second selected card to any players located at the plurality of playing positions disposed around the game surface; and a processor in communication with the first card reader and the first display device as well as the second card reader and the second display device such that the indicia of the first card can be automatically displayed on the first display device upon being read by the first card reader and the indicia of the second card can be automatically displayed on the second display device upon being read by the second card reader.

2. The system of claim 1, wherein each of the first defined set of cards includes a unique RFID tag associated therewith.

3. The system of claim 2, wherein each of the second defined set of cards includes a unique RFID tag associated therewith.

4. The system of claim 2, wherein the first card reader is an RFID reader that is configured to read the RFID tag associated with the first card to obtain the information.

5. The system of claim 3, wherein the second card reader is an RFID reader that is configured to read the RFID tag associated with the second selected card to obtain the information.

6. The system of claim 1, further comprising:
a plurality of player terminals that allow a player to place wagers on the first game of chance and/or the second game of chance.

7. The system of claim 6, wherein the outcome of the first game of chance is determined based on rules akin to the game of roulette.

8. The system of claim 7, wherein the outcome of the second game of chance is determined based on rules akin to the game of roulette.

9. The system of claim 6, wherein the outcome of the first game of chance is determined based on rules akin to the game of craps.

10. The system of claim 1, wherein the first card reader is a scanner that is configured to read a bar code associated with the first selected card.

11. The system of claim 10, wherein the second card reader is a scanner that is configured to read a bar code associated with the second selected card.

12. A table game system involving a plurality of games of chance, comprising:
a game surface having a plurality of player positions and a dealer position;
a first card shuffling machine disposed adjacent the dealer position for selecting a first card from a first set of cards, each card in the first set of cards having a unique RFID tag associated therewith, which contains information about indicia of the card;
a second card shuffling machine disposed adjacent the dealer position for selecting a second card from a second set of cards, each card in the second set of cards having a unique RFID tag associated therewith, which contains information about indicia of the card;
a first card reader associated with the first shuffling machine for obtaining from the first selected card, an indicia relevant to an outcome of a first game of chance, the first card reader is an RFID reader that is configured to read the RFID tag associated with the first card;
a second card reader associated with the second shuffling machine for obtaining from the second selected card an indicia relevant to an outcome of a second game of chance, the second card reader is an RFID reader that is configured to read the RFID tag associated with the second card;
a processor in communication with the first card reader to receive the indicia of the first selected card and configured to determine the outcome of the first game of chance based on that indicia; the processor in communication with the second card reader to receive the indicia of the second card and configured to determine the outcome of the second game of chance based on that indicia;
a plurality of terminals in communication with the processor and configured to receive wagers on at least one of the first game of chance or the second game of chance.

13. The system of claim 12, wherein the plurality of terminals are configured to receive wagers on both the first game of chance and the second game of chance.

14. The system of claim 13, wherein based on the determined outcomes of the first game of chance and the second game of chance, the processor resolves the wagers received at the plurality of terminals.

15. The system of claim 12, wherein the outcome of the first game of chance is determined based on rules akin to the game of roulette.

16. The system of claim 12, wherein the outcome of the second game of chance is determined based on rules akin to the game of roulette.

17. The system of claim 12, wherein the outcome of the first game of chance is determined based on rules akin to the game of craps.

18. The system of claim 12, wherein the first card reader is a scanner that is configured to read a bar code associated with the first selected card.

19. The system of claim 18, wherein the second card reader is a scanner that is configured to read a bar code associated with the second selected card.

20. The system of claim 12, wherein each of the plurality of terminals includes a touch screen display that is configured to allow for the input of wagers by a user.

21. The system of claim 20, further composing:
a tip button located on the display screen that allows the user to place a tip for a Dealer.

22. A method comprising:
rotating a first shuffling machine that houses a defined first set of cards;
selecting a single first card from the defined first set of cards;
rotating a second shuffling machine that houses a defined second set of cards;
removing the single first card from the first shuffling machine;
electronically identifying an indicia of the single first card such that an outcome of a first game of chance can be determined;
resolving wagers associated with the first game of chance;
selecting a single second card from the defined second set of cards;
removing the single second card from the second shuffling machine;
electronically identifying via an indicia of the single second card such that an outcome of a second game of chance can be determined;
resolving wagers associated with the second game of chance; and
again rotating the first shuffling machine in connection with a replay of the first game of chance.

23. The method of claim 22, further composing:
providing a plurality of terminals that are configured to receive wagers on the outcome of at least one of the first game of chance or the second game of chance.

24. The method of claim 22, further comprising:
providing a plurality of terminals that are configured to receive wagers on the outcomes of both the first game of chance and the second game of chance.

25. The method of claim 22, further comprising:
   automatically resolving the wagers on the outcome of the first game of chance.

26. The method of claim 25, further composing:
   automatically resolving the wagers on the outcome of the second game of chance.

27. The method of claim 22, wherein the step of electronically identifying the selected first card includes reading a unique RFID tag associated with the selected first card that contains information about its indicia.

28. The method of claim 27, wherein the step of electronically identifying the selected second card includes reading a unique RFID tag associated with the selected second card that contains information about its indicia.

29. The method of claim 22, wherein the outcome of the first game of chance is determined based on rules akin to the game of roulette.

30. The method of claim 29, wherein the outcome of second game of chance is determined based on rules akin to the game of roulette.

31. The method of claim 22, wherein the outcome of the first game of chance is determined based on rules akin to the game of craps.

32. The method of claim 23, further comprising:
   providing a tip button on a touch screen display of the plurality of terminals to that is configured to allow a user to tip a Dealer.

* * * * *